(12) United States Patent
Clark et al.

(10) Patent No.: US 8,359,083 B2
(45) Date of Patent: Jan. 22, 2013

(54) MICROELECTRODE ARRAY SYSTEM WITH INTEGRATED REFERENCE MICROELECTRODES TO REDUCE DETECTED ELECTRICAL NOISE AND IMPROVE SELECTIVITY OF ACTIVATION

(75) Inventors: Gregory Arthur Clark, Salt Lake City, UT (US); David J. Warren, Salt Lake City, UT (US); Noah M. Ledbetter, Salt Lake City, UT (US); Marcy Lloyd, Milwaukee, WI (US); Richard A. Normann, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 719 days.

(21) Appl. No.: 12/417,530

(22) Filed: Apr. 2, 2009

(65) Prior Publication Data

US 2009/0283425 A1    Nov. 19, 2009

Related U.S. Application Data

(60) Provisional application No. 61/041,819, filed on Apr. 2, 2008.

(51) Int. Cl.
*A61B 5/0478*    (2006.01)
*A61N 1/05*    (2006.01)
*A61B 5/0484*    (2006.01)

(52) U.S. Cl. ........ 600/378; 600/373; 600/393; 600/544; 607/117; 607/118

(58) Field of Classification Search .......... 600/372, 600/373, 378, 383, 393, 544–545, 546
See application file for complete search history.

(56) References Cited

U.S. PATENT DOCUMENTS

| | | | | |
|---|---|---|---|---|
| 4,969,468 A | * | 11/1990 | Byers et al. | 600/373 |
| 5,215,088 A | * | 6/1993 | Normann et al. | 600/377 |
| 5,388,577 A | * | 2/1995 | Hubbard | 600/377 |
| 5,411,537 A | | 5/1995 | Munshi et al. | |
| 5,443,559 A | * | 8/1995 | Chen et al. | 600/396 |
| 5,824,027 A | | 10/1998 | Hoffer et al. | |
| 6,032,072 A | | 2/2000 | Greenwald et al. | |
| 6,091,975 A | * | 7/2000 | Daddona et al. | 600/345 |
| 6,132,683 A | | 10/2000 | Sugihara et al. | |
| 6,622,035 B1 | * | 9/2003 | Merilainen et al. | 600/391 |
| 6,782,283 B2 | * | 8/2004 | Schmidt et al. | 600/372 |
| 7,536,227 B1 | | 5/2009 | Poore et al. | |
| 2004/0040868 A1 | | 3/2004 | DeNuzzio et al. | |
| 2006/0135862 A1 | * | 6/2006 | Tootle et al. | 600/373 |

(Continued)

FOREIGN PATENT DOCUMENTS

EP    1 278 064    7/2008
WO    WO 2007/115694    10/2007

OTHER PUBLICATIONS

U.S. Appl. No. 12/635,374, filed Dec. 10, 2009; Gregory Arthur Clark; office action issued Mar. 26, 2012.

*Primary Examiner* — Lee S Cohen
*Assistant Examiner* — Erin M Cardinal
(74) *Attorney, Agent, or Firm* — Thorpe North & Western LLP

(57) ABSTRACT

A microelectrode array system used to sense physiological signals and stimulate physiological tissue to form signals is disclosed. The array includes a dielectric substrate and a two dimensional array of signal microelectrodes substantially perpendicular to and integrated on the dielectric substrate. At least one reference microelectrode is located adjacent to and integrated with the signal microelectrodes on the dielectric substrate. The reference microelectrodes are positioned on the dielectric substrate relative to the signal microelectrodes to enable a reduced level of electrical noise to be detected between the reference microelectrodes and the recording microelectrodes.

20 Claims, 4 Drawing Sheets

U.S. PATENT DOCUMENTS

| | | | |
|---|---|---|---|
| 2006/0173259 A1* | 8/2006 | Flaherty et al. | 600/331 |
| 2007/0067007 A1* | 3/2007 | Schulman et al. | 607/115 |
| 2007/0142889 A1 | 6/2007 | Whitehurst et al. | |
| 2008/0138583 A1 | 6/2008 | Bhandari et al. | |
| 2010/0041972 A1* | 2/2010 | Mason | 600/372 |

\* cited by examiner

43

Implanting an array of signal microelectrodes integrated on a dielectric substrate into a patient such that the signal microelectrodes are proximate to at least one of neural tissue and nerve tissue, said array having a plurality of reference microelectrodes integrated onto the dielectric substrate sufficient to enable a reduced level of electrical noise to be detected between the reference microelectrodes and the signal microelectrodes. — 42

Performing at least one of sensing the physiological signals between at least one signal microelectrode and at least one reference microelectrode and stimulating the signals in the conductive complex physiological solution by injecting a current between at least one signal microelectrode and at least one reference microelectrode. — 44

FIG. 3

MICROELECTRODE ARRAY SYSTEM WITH INTEGRATED REFERENCE MICROELECTRODES TO REDUCE DETECTED ELECTRICAL NOISE AND IMPROVE SELECTIVITY OF ACTIVATION

RELATED APPLICATIONS

This application claims the benefit of U.S. Provisional patent application Ser. No. 61/041,819, filed on Apr. 2, 2008 and which is incorporated herein by reference.

This application is related to U.S. patent application Ser. No. 11/807,764, filed May 29, 2007 entitled "WAFER SCALE NEEDLE ARRAY", U.S. patent application Ser. No. 11/807,763, filed May 29, 2007, entitled "MASKING HIGH ASPECT-RATIO STRUCTURES", U.S. patent application Ser. No. 11/807,766, filed May 29, 2007, entitled "MICRO-NEEDLE ARRAYS HAVING NON-PLANAR TIPS AND METHODS OF MANUFACTURE THEREOF", and U.S. Provisional Patent Application Ser. No. 61/121,473, filed Dec. 10, 2008, entitled "AN ELECTRICALLY SHIELDED CONTAINMENT SYSTEM FOR A HIGH COUNT MICROELECTRODE ARRAY TO REDUCE DETECTED ELECTRICAL NOISE", each of which are hereby incorporated by reference.

GOVERNMENT RIGHTS

This invention was made with government support under the Department of Defense, Defense Advanced Research Projects Agency Revolutionizing Prosthetics program, Contract No. N66001-06-C-8005, via a subcontract from the Johns Hopkins University Applied Physics Laboratory. The government has certain rights to this invention.

BACKGROUND

1. Field of the Invention

The present invention relates generally to microelectrode array devices and methods of detecting physiological signals within a body.

2. Related Art

The potential for implanting electronic devices into patients with direct interface to the neural system is vast. Systems which may enable paraplegics to regain control of their bladder or limbs, provide vision for the blind, or restore vocal cord function are all under development, and promising initial results have been obtained in some experiments.

A key component of some implantable systems is a needle array to enable interfacing of the electronics with a nerve or directly with neuron in brain tissue. For example, U.S. Pat. No. 5,215,088 to Norman et al. discloses a three-dimensional electrode device which can be used as a neural or cortical implant. The device of Norman, also known as the Utah Electrode Array (UEA), can be used to provide a neural interface to electronic equipment for sensing and/or stimulation of physiological signals and pathways and has been successfully used in a large number of patients. However, difficulties and challenges of this system are still present which limit its effectiveness and potential applications. Biological organisms, from the simple to the substantially complex, can include a wide range of different physiological signals and pathways for the signals to travel. The large number of different signals and pathways can cause biological organisms to be a relatively noisy electrical environment. Neural and nerve impulses tend to have a relatively low amplitude in comparison to surrounding competing signals from other physiological systems, e.g. muscles. Accurately sensing and/or activating these signals and pathways within this noisy environment can be challenging.

SUMMARY

A microelectrode array system used to sense signals and stimulate physiological tissue to form signals is disclosed. The array includes a dielectric substrate and a two dimensional array of signal microelectrodes substantially perpendicular to and integrated on the dielectric substrate. One or more reference microelectrodes are located adjacent to and integrated with the signal microelectrodes on the dielectric substrate. The reference microelectrodes are positioned on the dielectric substrate relative to the recording and/or stimulating microelectrodes to enable a reduced level of electrical noise to be detected between the reference microelectrodes and the recording microelectrodes, or to enable more focal bipolar or multipolar stimulation, relative to monopolar stimulation to a distal reference point.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 3 is a flow chart illustrating use of the system in accordance with one embodiment of the present invention.

It will be understood that these figures are provided merely for convenience in describing the invention and are drawn for purposes of clarity rather than scale. As such, actual dimensions may, and likely will, deviate from those illustrated in terms of relative dimensions, contours, and the like. For example, FIG. 2c illustrates an embodiment showing a microelectrode array with 13 electrodes along a side. The array may vary from a few electrodes to hundreds or even thousands along a side.

DETAILED DESCRIPTION OF EXAMPLE EMBODIMENTS

Figure 1A:
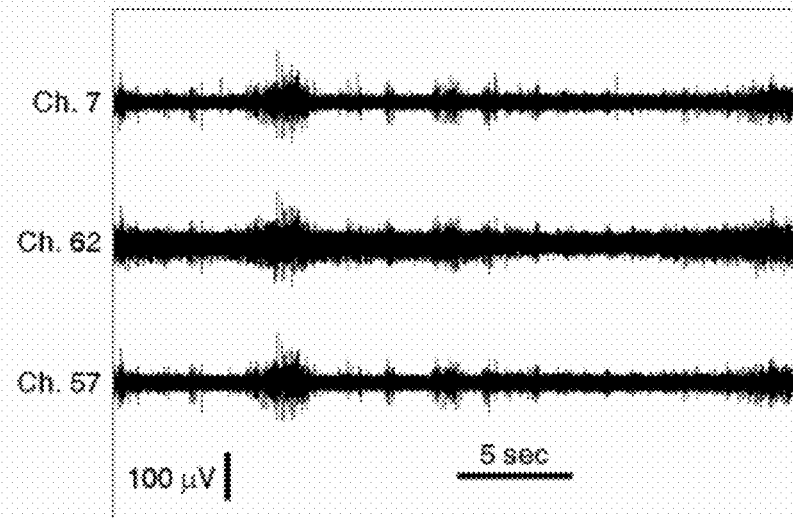
FIG. 1a is a graph showing electrical measurements of a nerve with a reference electrode implanted in surrounding muscle tissue.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

In describing embodiments of the present invention, the following terminology will be used.

The singular forms "a," "an," and "the" include plural referents unless the context clearly dictates otherwise. Thus, for example, reference to "a needle" includes reference to one or more of such needles and "etching" includes one or more of such steps. Similarly, the plural forms include singular referents unless the context clearly dictates otherwise.

As used herein, "substantial" when used in reference to a quantity or amount of a material, or a specific characteristic thereof, refers to an amount that is sufficient to provide an effect that the material or characteristic was intended to provide. Therefore, "substantially free" when used in reference to a quantity or amount of a material, or a specific characteristic thereof, refers to the absence of the material or characteristic, or to the presence of the material or characteristic in an amount that is insufficient to impart a measurable effect, normally imparted by such material or characteristic.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50-250 micrometers should be interpreted to include not only the explicitly recited values of about 50 micrometers and 250 micrometers, but also include individual values and sub-ranges within the indicated range. Thus, included in this numerical range are individual values such as 60, 70, and 80 micrometers, and sub-ranges such as from 50-100 micrometers, from 100-200, and from 100-250 micrometers, etc. This same principle applies to ranges reciting only one numerical value and should apply regardless of the breadth of the range or the characteristics being described.

In the present disclosure, the term "preferably" or "preferred" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

As used herein, the terms "about" or "approximately" mean that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the terms "about" and "approximately" shall expressly include "exactly," consistent with the discussion above regarding ranges and numerical data.

As used herein, the term "signal electrode(s)" may refer to an electrode or electrodes used for recording, stimulation, or both.

As mentioned above, accurately sensing signals within the relatively noisy electrical environment of a biological organism can be challenging. However, accurate sensing of signals and/or stimulation of physiological tissue to form signals can provide for effective strategies for repairing or replacing nervous system components within a biological organism. For example, a fundamental challenge for effective motor and sensory neuro-prostheses is selective activation: the ability to activate specific nerve fibers, while sparing or inhibiting others. To provide effective control, one should be able to communicate specific instructions to the nervous system without also issuing contradictory or interfering commands. Present-day electric interfaces offer only limited capabilities for selective activation, thereby limiting the ability to restore function.

Additionally, accurate measurements of physiological signals within a body can be used to provide control of artificial and biological devices. For example, measurements of motor neural signals sent to or travelling down a nerve within a body can be used to control an artificial device such as an artificial appendage, or distal body parts. Similarly, sensory information travelling along sensory nerve fibers or elsewhere can be detected and then used to provide cutaneous, proprioceptive, or other types of sensory feedback and information to an individual. These neural signals can be relatively small, on the order of tens to hundreds of microvolts, requiring a low level of background noise in order for the signals to be accurately detected. Hence, in order for the signal to be accurately detected, interpreted, and communicated, it can be helpful to reduce or eliminate various types of electrical noise, such as electrical noise that occurs within a body, emanates from outside the body (e.g., 60-Hz power-line noise), or emanates from another location within the body (e.g., electrical signals from heart or muscle). The reduction or elimination of these types of electrical noise can significantly enhance the ability to record electrical discharges of selected neurons or axons.

For example, FIG. 1a illustrates a measurement made using a variation of the Utah Electrode Array (UEA), referred to as the Utah Slanted Electrode Array (USEA). The USEA includes a two dimensional array of microelectrodes integrated on a dielectric substrate. The microelectrodes are positioned substantially perpendicular to the substrate. The rows have a progressively decreasing height with respect to the dielectric substrate. The variation in the height of the electrodes can allow measurement of different types of neuronal action potentials. The USEA was implanted into the sciatic nerve of a feline. According to the conventional approach, a discrete metal wire electrode was placed in the muscular tissue surrounding the sciatic nerve to act as a reference electrode. The USEA was then activated to receive neural recordings of active signals within the sciatic nerve. However, electromyogram (EMG) signals from the surrounding muscle tissue provide significant noise on all three channels recorded within the sciatic nerve. It can be difficult to distinguish the neural signals from the background noise in the surrounding tissue.

Figure 1B:
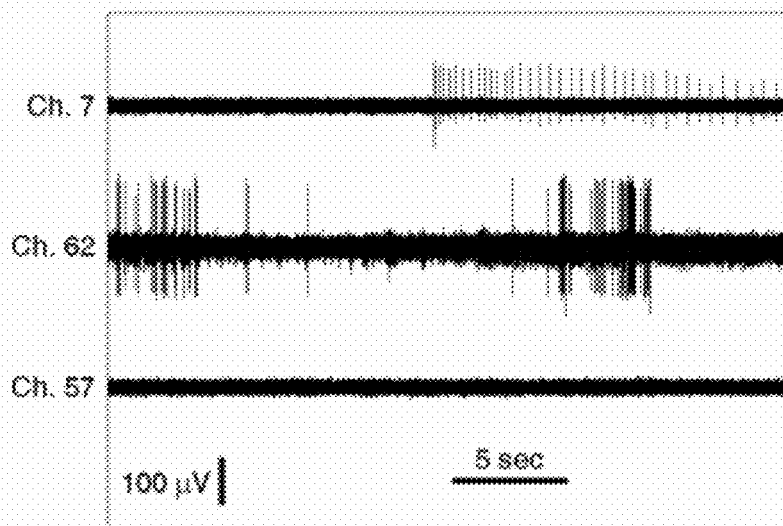
FIG. 1b is a graph showing electrical measurements of the nerve in FIG. 1a with reference electrodes integrated with signal electrodes in accordance with an embodiment of the present invention.

FIG. 1b illustrates the same measurement using a plurality of large tipped reference electrodes located in the array. The reference electrodes are integrated on the dielectric substrate with the measurement electrodes, rather than using a discrete wire as a reference electrode. Additionally, a flexible, electrically grounded shield was also used as part of a containment system around the array. Channels 7 and 62 in FIG. 1b, representing two of the microelectrodes in the array, show neural activity that is recorded within the sciatic nerve. With the reduction in noise it can be seen that no neural activity is detected on channel 57. In contrast, it is not possible to determine whether or not neural activity is present on channel 57 in FIG. 1a due to the relatively large amount of background noise. The neural activity recorded in FIG. 1b has a substantially reduced level of noise from EMG signals in the surrounding tissue. The reduced level of noise enables the neural signals to be easily distinguished from the background noise.

Figure 2A:
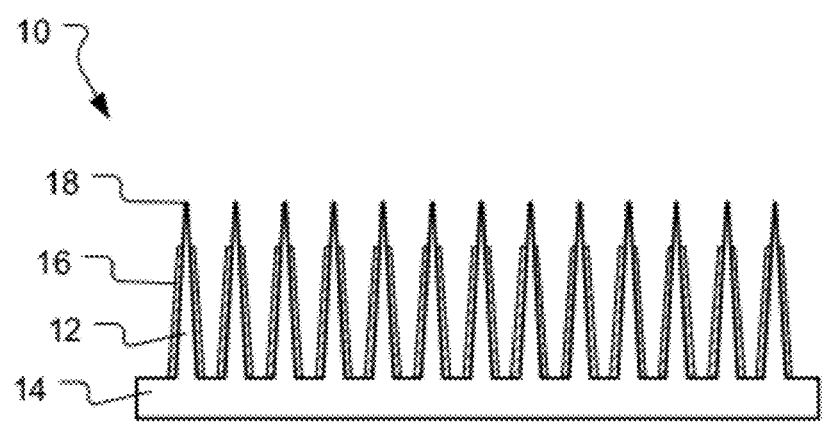
FIG. 2a is a side view of an illustration of a microelectrode array with electrodes having substantially equal height.

One exemplary embodiment of the microelectrode array is illustrated in FIG. 2a. The array can include an array of micro-electrodes 12 extending upward from the dielectric substrate 14. Typically, each of the micro-electrodes is individually addressable, i.e. separated from one another via a dielectric material such as epoxy or glass. The dielectric substrate can be a silicon wafer, enabling a plurality of arrays to be formed at one time using known lithographic and/or micromachining techniques. The two dimensional array of electrodes may be formed from a single substrate. Alternatively, a plurality of microelectrodes formed on different substrates can be coupled together to form the array. A typical microelectrode array, such as the UEA, can include a 10×10 array of electrodes, although the array is not limited to a small number of electrodes. Nor is the array necessarily square. A different number of electrodes may be formed in each of the two dimensions, such as an array of 100×200 electrodes. The microelectrode array may include hundreds to thousands of micro-electrodes in each dimension of the array.

The electrodes can optionally include a coating 16. In one aspect, this coating can be an insulating material such as, but not limited to, parylene-C, silicon carbide, ceramics, or other insulating polymers. The coating can be removed from the tips 18 of the electrodes, enabling the tips to be electrically conductive. The coating can be removed using etching, laser ablation, or other suitable method that enables a predetermined portion of each electrode to be substantially free of the coating. The coating can reduce cross-talk between the electrodes and concentrate electric potential around a desired neuron or nerve. The coating can also reduce the level of background noise that is received by the microelectrodes.

The electrodes in a microelectrode array are typically manufactured to come to a point at the top. At the base, the electrodes may be circular, oval, square, rectangular, or have an irregular shape. In one embodiment, each electrode is independently electrically addressable. This enables a specific signal to be transmitted through a desired electrode. In another embodiment, the array can be addressed by column or row. In yet another embodiment, the entire array can be electrically connected such that a single signal can be sent through the electrodes in the array.

Figure 2B:
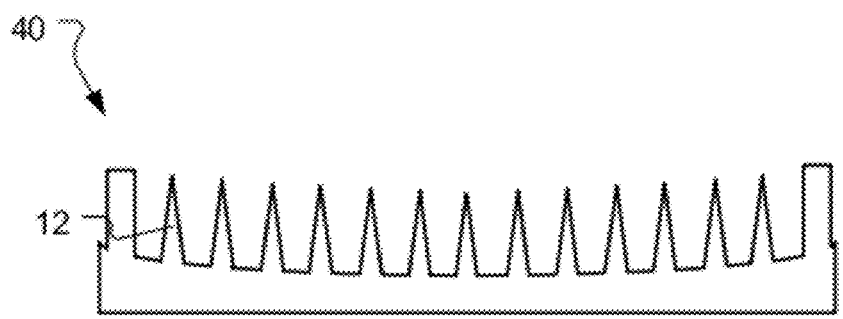
FIG. 2b is a side view of an illustration of a microelectrode array with electrodes having varying heights.
Figure 2C:
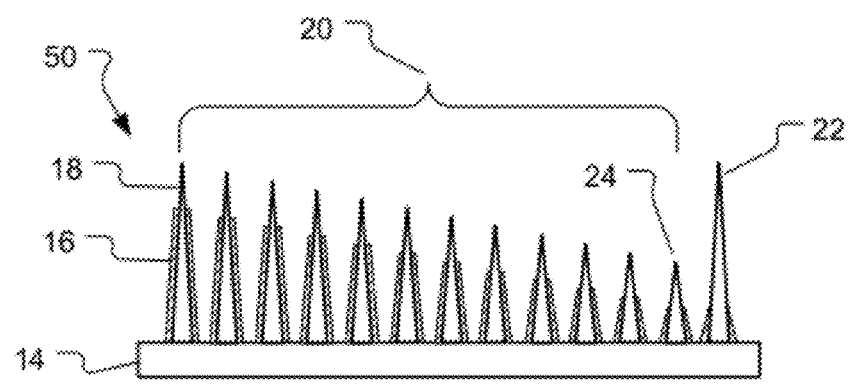
FIG. 2c is a side view of an illustration of a microelectrode array with rows of signal electrodes having progressively decreasing height and a reference electrode row adjacent a shortest row of the signal microelectrodes in accordance with an embodiment of the present invention.

In one embodiment, the microelectrode array 10 can be configured such that each of the micro electrodes 12 has a substantially uniform height relative to the substrate 14. In another embodiment, the micro-electrodes may vary in height. For example, FIG. 2b illustrates a microelectrode array 40 with the micro electrodes 12 configured to vary in height with a spherical concave shape. Similarly, FIG. 2c illustrates a microelectrode array 50 with each row having a progressively decreasing height with respect to the dielectric substrate 14. As previously discussed, this variation in height in the electrodes can increase the number of signals that can be sensed and the types of tissue that can be stimulated using the array when it is interfaced with tissue within a body, such as a muscle, a nerve, the brain, and so forth. FIG. 2c illustrates a plurality of rows of signal microelectrodes 20 and a row of reference microelectrodes 22 located adjacent the shortest row 24 of signal microelectrodes. As used herein, the term signal microelectrode is intended to include one or more microelectrodes that are configured to sense signals in a complex physiological solution. The term signal microelectrodes or signal electrodes can also be used to include one or more microelectrodes that are configured to provide an electrical potential to stimulate tissue to form signals in the complex physiological solution. In one embodiment, a signal microelectrode may be able to both sense a signal and stimulate tissue to form a signal. In another embodiment, a signal microelectrode may be specifically configured to either sense signals or stimulate tissue.

The reference 22 and signal 20 microelectrodes can be formed from a single substrate 14. Alternatively, they can be formed on different substrates and coupled to form a single array. The reference and signal microelectrodes can be substantially perpendicular to the substrate. Constructing the microelectrodes to be perpendicular to the substrate provides mechanical strength to the electrodes, enabling the array to be implanted in various kinds of tissue with minimal damage to the electrodes during insertion and use.

In one embodiment, the reference microelectrodes 22 can be located in a single row, as illustrated in FIG. 2c. In another embodiment, multiple rows of reference microelectrodes may be formed on the substrate 14. Alternatively, the reference microelectrodes may be located at the corners of the array, around the perimeter of the array, at the center of the array, or alternating between signal microelectrodes 20 within the array.

The actual positioning of the reference microelectrodes 22 relative to the signal microelectrodes 20 depends upon the particular use of the microelectrode array and the desired type of signal sensing or stimulus being performed. The reference microelectrodes may be positioned to minimize the level of electromagnetic interference and background signals that are received at the signal microelectrodes. For example, placing the reference microelectrodes in a row or column or along a perimeter of the array can help to reduce the level of EMG signals, as illustrated in FIG. 1b.

Various methods have been developed to apply the coating 16 of insulating material over the microelectrodes while leaving the tips 18 of the electrodes substantially exposed to enable signals to be sensed and stimulated. For example, U.S. patent application Ser. No. 11/807,763, entitled "MASKING HIGH ASPECT-RATIO STRUCTURES" discloses a method for using lithographic processes to remove the insulating material from the tips. This process works especially well at exposing a plurality of tips over a relatively straight line. Thus, the process enables a tip of relatively equal height to be exposed over the array with progressively decreasing height, as shown in FIG. 2c.

However, unlike the signal microelectrodes 20, the inventors have found that the function of the reference electrodes 22 is improved when a greater surface area of the reference electrodes is exposed relative to the exposure of the signal electrodes. A greater amount of exposed area on the reference microelectrode enables the reference microelectrode to have a lower impedance, compared with the impedance of a typical recording electrode, for example, which may have an impedance of tens or even hundreds of Kohms (measured at 1 KHz). Substantially removing the coating 16 from the reference electrode(s) 22 can provide a reference electrode with an impedance approaching a value of zero ohms. The relatively low impedance of the reference electrode(s) can substantially increase the accuracy of the signal recorded by the signal electrodes relative to the reference electrode(s).

Thus, it has been discovered that a substantial portion of the insulative coating 16 can be removed from the reference electrodes 22 by placing one or more rows of reference electrodes adjacent to the shortest row 24 of signal electrodes 20. The same process can be used to substantially bare the tips 18 of the signal electrodes to a desired height while also substantially removing the insulative coating from the reference electrodes, thereby maximizing the surface area of the reference electrodes while maintaining the tip size of the array of signal electrodes having decreasing height. This allows the microelectrode array with integrated reference electrodes to be manufactured without additional steps needed to produce the reference electrodes having a relatively large conductive surface area. In one embodiment, the row(s) of reference electrodes can be substantially the same height as the tallest row of signal electrodes. In another embodiment, the reference electrodes can have a greater height than any of the signal electrodes with respect to the substrate 14.

The exposed portion of the reference electrodes 22 may be coated with a conductive material such as a metal or alloy to provide greater conductivity. The signal microelectrode tips 18 may also be coated with a selected conductive or biological material to enable the tips to sense or stimulate a desired physiological signal.

The reference electrodes 22 on the microelectrode array 50 can be used to measure potential or to apply a current. When the signal electrodes 20 are used to sense a physiological signal within a body, the reference electrodes can be used as an electrical reference for the signal measured by the signal electrodes. Thus, the electrical potential or voltage can be measured between one or more signal microelectrodes and one or more reference microelectrodes.

The signal microelectrodes 20 can also be used to inject a current, with one or more signal microelectrodes acting as a cathode (source) and one or more reference microelectrodes 22 acting as an anode (return), or vice versa. When the reference electrodes are acting as a return and are located relatively distant from the stimulating electrode, the result is referred to as monopolar stimulation. For example, monopolar stimulation may be accomplished when the signal microelectrodes and the reference microelectrodes are located on or near opposite sides of the array. When the reference electrode is acting as a return and is located relatively close to the signal electrodes acting as a source, such as adjacent to the stimulating electrode, the result is referred to as bipolar stimulation. Various combinations of electrodes can be used to produce multipolar stimulation, allowing focusing and steering of currents. Monopolar, bipolar, and multipolar stimulation can be used to activate and deactivate various physiological pathways within the body.

The signal microelectrodes 20 are typically independently addressable, enabling signals to be measured and applied at each signal microelectrode. However, it may be beneficial to electrically connect two or more of the signal microelectrodes. The reference microelectrodes 22 may also be electrically isolated from adjoining reference microelectrodes. Alternatively, the reference microelectrodes may be connected together in series or parallel.

Connecting the reference microelectrodes together can create a common reference with a larger surface area. One or more rows of reference microelectrodes that are interconnected may also be used to provide additional radio frequency shielding to the signal microelectrodes. The row(s) of reference microelectrodes may further act as a partial faraday cage, shielding the signal microelectrodes from signals that radiate through the tissue in which they are implanted, thereby helping to isolate the signal electrodes from physiological signals generated in surrounding tissue. Additional shielding can also be placed around the microelectrode array when it is implanted, such as a flexible electrically grounded shield that can be used to help minimize noise detected from surrounding tissue or physiological processes. Various exemplary configurations for such shielding are further described in related U.S. Provisional Patent Application Ser. No. 61/121,473.

The integration of reference electrodes 22 into the array of microelectrodes 50 can enable bio-based selective stimulation that can mimic normal physiological activation patterns within a body. For example, specific fibers within a nerve can be activated while sparing or inhibiting activation in other fibers. Selective activation can enable effective neuro-motor control. Fibers within a given nerve can act as wire bundles within the body. Different fibers within a nerve bundle can go to different (and sometimes opposing) muscles. An implanted array of microelectrodes with integrated microelectrodes can provide selective activation of certain muscle groups, selective activation of fibers within a muscle, and selective inhibition of other muscle groups. This capability may provide excellent control of skeletal muscles used in voluntary movement, or other types of muscle including but not limited to smooth muscle, such as muscles involved in bladder control.

The microelectrode array can also be used to activate specific fiber types within a muscle according to the normal physiologic order, in order to produce finely graded, fatigue resistant responses. Additionally, unlike skeletal muscles, smooth muscles (such as the bladder) receive both excitation and inhibition signals. Hence, it is necessary to turn off one set of neural inputs selectively, while selectively turning on the other. Conventional nerve cuff electrodes and stimulation techniques are relatively ineffective at achieving selective activation.

Activation of specific types of fibers within a muscle can be important to reducing fatigue. For example, the calf (gastrocnemius) muscle is composed of both slow, small weak, fatigue-resistant (S) type fibers, and large, powerful, fast fatigable (FF) fibers. It is important to activate the S fibers first, as occurs in normal physiology, in order to achieve finely graded, fatigue resistant responses. But because large fibers are easier to activate with extracellular currents, conventional stimulation techniques typically produce the reverse, inappropriate recruitment order. Selective deactivation can be used to overcome this limitation.

Selective deactivation can also be used to block undesired, spontaneous activity in nerve fibers. Spontaneous activity (or evoked, pseudo-spontaneous activity) can be blocked by sending a neural signal from the microelectrode array to collide with and effectively cancel out the original, undesired nerve impulse.

In another embodiment, a method 40 of sensing physiological signals and stimulating signals in a complex physiological solution is disclosed, as depicted in the flow chart of FIG. 3. The method includes the operation of implanting 42 an array of signal microelectrodes integrated on a dielectric substrate into a patient such that the signal microelectrodes are proximate to at least one of neural tissue and nerve tissue.

The array can have a plurality of reference microelectrodes integrated onto the dielectric substrate sufficient to enable a reduced level of electrical noise to be detected between the reference microelectrodes and the signal microelectrodes. The method further includes the operation of sensing the physiological signals between at least one of the signal microelectrodes and at least one of the reference microelectrodes. Alternatively, the operation can include stimulating the signals in the conductive complex physiological solution by injecting a current between the at least one signal microelectrode and the at least one reference microelectrode.

Summarizing and reiterating to some extent, a microelectrode array system used to sense and stimulate physiological signals has been developed. The microelectrode array includes a two dimensional array of signal microelectrodes integrated on a dielectric substrate. One or more reference microelectrodes are located adjacent to and integrated with the signal microelectrodes on the dielectric substrate. The reference microelectrodes can be positioned in the array to reduce the level of electrical noise that is detected between the reference microelectrodes and the signal microelectrodes. The reference microelectrodes can also be used to enable the signal microelectrodes to selectively activate and deactivate nerve fibers, muscle fibers, and other types of electrical pathways within the body.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

What is claimed is:

1. A microelectrode array system used to sense physiological signals and stimulate signals in a conductive complex physiological solution, comprising:
    a dielectric substrate;
    a two dimensional array of signal microelectrodes substantially perpendicular to and integrated on the dielectric substrate, wherein each signal microelectrode in the array has a predetermined height relative to the dielectric substrate, wherein the signal microelectrodes are substantially coated with an insulative material to reduce the level of electrical noise received by the signal microelectrodes and have exposed uninsulated tips configured to perform at least one of sensing the physiological signals and stimulating signals in the conductive complex physiological solution; and
    at least one reference microelectrode located adjacent to and integrated with the signal microelectrodes on the dielectric substrate, wherein the at least one reference microelectrode is positioned on the dielectric substrate relative to the signal microelectrodes to enable a reduced level of electrical noise to be detected between the reference microelectrode and the signal microelectrodes, wherein the at least one reference microelectrode has a greater exposed uninsulated surface area relative to the exposed tips of each of the signal microelectrodes, and wherein the at least one reference microelectrode measures potential and is used as an electrical reference for the signal measured by the signal microelectrodes.

2. The system of claim 1, wherein, the at least one reference micro electrode is substantially free of the insulative material to enable the reference microelectrodes to have an impedance of substantially zero ohms.

3. The system of claim 1, wherein the at least one reference microelectrode includes a plurality of reference microelectrodes that are positioned on the dielectric substrate relative to the signal microelectrodes to provide electrical shielding to enable a reduced level of electromyogram signals detected between the signal microelectrodes and the reference microelectrodes.

4. The system of claim 1, wherein the at least one reference microelectrode includes a plurality of reference microelectrodes that are electrically connected in parallel to provide electrical shielding to the array of signal microelectrodes.

5. The system of claim 1, wherein the at least one reference microelectrode includes a plurality of reference electrodes that are positioned in a column adjacent the two dimensional array of signal microelectrodes to provide electrical shielding to the array of signal microelectrodes.

6. The system of claim 1, wherein the two dimensional array of signal microelectrodes includes rows of microelectrodes of varying height with respect to the dielectric substrate.

7. The system of claim 1, wherein the two dimensional array of signal microelectrodes includes rows of signal microelectrodes of progressively decreasing height with respect to the dielectric substrate.

8. The system of claim 7, wherein the at least one reference microelectrode includes a plurality of reference microelectrodes that are positioned in a column adjacent a shortest column of signal microelectrodes in the two dimensional array and the reference electrodes are substantially longer than the shortest row of signal electrodes.

9. The system of claim 8, wherein both the column of reference microelectrodes and the shortest column of signal microelectrodes, located adjacent to the column of reference microelectrodes, include a sleeve of insulative material, with the sleeve having a substantially equal height on each of the reference microelectrodes and the shortest signal microelectrodes.

10. The system of claim 1, wherein the at least one reference microelectrode is coated with a conductive material to increase a conductivity of the reference microelectrode.

11. The system of claim 1, wherein the at least one reference microelectrode includes a plurality of reference electrodes that are positioned at outer corners of the two dimensional array of signal microelectrodes to provide electrical shielding to the array of signal microelectrodes.

12. The system of claim 1, wherein the at least one reference microelectrode includes a plurality of reference microelectrodes that are positioned sufficiently remote from an active stimulating electrode in the two dimensional array of signal microelectrodes to provide monopolar stimulation.

13. The system of claim 1, wherein the at least one reference microelectrode is positioned adjacent to an active stimulating electrode in the two dimensional array of signal microelectrodes to provide bipolar stimulation.

14. The system of claim 1, wherein the signal microelectrodes in the two dimensional array are individually electrically addressable.

15. The system of claim 1, wherein the signal electrodes and the at least one reference electrode are penetrating electrodes.

16. A method of performing at least one of sensing physiological signals or stimulating signals in a complex physiological solution, comprising:
    implanting the system of claim 1 into a patient such that the signal microelectrodes are proximate to at least one of neural tissue or nerve tissue; and
    performing at least one of sensing the physiological signals between at least one of the signal microelectrodes and the at least one reference microelectrode, or stimulating the signals in the conductive complex physiological solution by injecting a current between at least one of the signal microelectrodes and the at least one reference microelectrode.

17. The method of claim 16, further comprising the step of stimulating, wherein the stimulating further comprises selectively deactivating a nerve signal by sending a neural signal from the signal microelectrodes to collide with and effectively cancel out an original, undesired nerve impulse.

18. The method of claim 16, further comprising the step of stimulating, wherein the stimulating further providing monopolar stimulation by sending a signal from at least one of the signal microelectrodes located on a first side of the microelectrode array relative to a reference microelectrode located on a substantially opposite side of the microelectrode array.

19. The method of claim 16, further comprising the step of stimulating, wherein the stimulating includes at least one of bipolar and multipolar stimulation to enable various combinations of stimulation useful for focal stimulation and blocking and steering currents.

20. The method of claim 17, wherein the signal electrodes and the at least one reference electrode are penetrating electrodes.

* * * * *

UNITED STATES PATENT AND TRADEMARK OFFICE
CERTIFICATE OF CORRECTION

| | | |
|---|---|---|
| PATENT NO. | : 8,359,083 B2 | Page 1 of 1 |
| APPLICATION NO. | : 12/417530 | |
| DATED | : January 22, 2013 | |
| INVENTOR(S) | : Clark et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 845 days.

Signed and Sealed this
Eighteenth Day of November, 2014

Michelle K. Lee
*Deputy Director of the United States Patent and Trademark Office*